(12) United States Patent
Hwang et al.

(10) Patent No.: US 10,017,743 B2
(45) Date of Patent: Jul. 10, 2018

(54) MDCK-DERIVED CELL STRAIN SUSPENSION-CULTURED IN PROTEIN-FREE MEDIUM AND METHOD FOR PROLIFERATING VIRUS USING CELL STRAIN

(71) Applicant: MOGAM BIOTECHNOLOGY INSTITUTE, Yongin-si, Gyeonggi-do (KR)

(72) Inventors: Mihee Hwang, Yongin-si (KR); Kukjin Park, Yongin-si (KR); Duckhyang Shin, Yongin-si (KR); Hyeon Lee, Yongin-si (KR); Sooin Kim, Yongin-si (KR); Eunyoung Cho, Yongin-si (KR); Misuk Kim, Yongin-si (KR); Dong Ho Ahn, Yongin-si (KR)

(73) Assignee: MOGAM BIOTECHNOLOGY INSTITUTE, Yongin-si (KR)

( * ) Notice: Subject to any disclaimer, the term of this patent is extended or adjusted under 35 U.S.C. 154(b) by 0 days.

(21) Appl. No.: 14/893,571

(22) PCT Filed: Jun. 3, 2014

(86) PCT No.: PCT/KR2014/004949
§ 371 (c)(1),
(2) Date: Nov. 24, 2015

(87) PCT Pub. No.: WO2014/196795
PCT Pub. Date: Dec. 11, 2014

(65) Prior Publication Data
US 2016/0108367 A1    Apr. 21, 2016

(30) Foreign Application Priority Data
Jun. 7, 2013  (KR) .................. 10-2013-0065229

(51) Int. Cl.
| C12N 7/00 | (2006.01) |
| A61K 39/00 | (2006.01) |
| A61K 39/145 | (2006.01) |
| A61K 39/12 | (2006.01) |
| C07K 14/005 | (2006.01) |
| C12N 5/071 | (2010.01) |

(52) U.S. Cl.
CPC ............ *C12N 5/0686* (2013.01); *A61K 39/12* (2013.01); *A61K 39/145* (2013.01); *C12N 7/00* (2013.01); *C12N 2500/92* (2013.01); *C12N 2760/16134* (2013.01); *C12N 2760/16151* (2013.01); *C12N 2760/16152* (2013.01); *C12N 2760/16234* (2013.01); *C12N 2760/16251* (2013.01); *C12N 2760/16252* (2013.01)

(58) Field of Classification Search
CPC ............ C12N 7/00; C12N 2760/16151; C12N 15/86; A61K 39/12; A61K 39/145
See application file for complete search history.

(56) References Cited

U.S. PATENT DOCUMENTS

| 2003/0044962 A1 | 3/2003 | Makizumi et al. |
| 2005/0118140 A1 | 6/2005 | Vorlop et al. |
| 2010/0010199 A1 | 1/2010 | Tsai et al. |
| 2011/0039330 A1 | 2/2011 | Price et al. |
| 2011/0097785 A1 | 4/2011 | Warthen et al. |
| 2012/0039939 A1 | 2/2012 | Shiloach et al. |
| 2013/0052717 A1 | 2/2013 | Liu et al. |
| 2013/0183741 A1 | 7/2013 | Park et al. |

FOREIGN PATENT DOCUMENTS

| JP | 2011-524182 A | | 9/2011 |
| KR | 10-2003-0032923 A | | 4/2003 |
| KR | 10-2005-0027165 A | | 3/2005 |
| KR | 1020050027165 | * | 3/2005 |
| KR | 10-2009-0057015 A | | 6/2009 |
| KR | 10-2012-0024464 A | | 3/2012 |
| WO | 97/37000 A1 | | 10/1997 |
| WO | 03/023025 A1 | | 3/2003 |
| WO | WO2012033328 | * | 3/2012 |
| WO | 2013/057715 A1 | | 4/2013 |

OTHER PUBLICATIONS

International Searching Authority International Search Report for PCT/KR2014/004949 dated Jul. 11, 2014.
Japanese Patent Office; Communication dated Dec. 7, 2016 in counterpart Japanese application No. 2016-518266.
European Patent Office; Communication dated Nov. 22, 2016, in counterpart European application No. 14807339.8.

* cited by examiner

*Primary Examiner* — Barry A Chestnut
(74) *Attorney, Agent, or Firm* — Sughrue Mion, PLLC

(57) ABSTRACT

The present invention relates to a novel MDCK-derived cell line capable of being suspension-cultured in a protein-free medium and a method for proliferating a virus using the MDCK-derived cell line to produce a vaccine. The novel MDCK-derived cell line exhibits high and uniform productivity for various viruses, while causing less viral antigenic variations with low tumorigenicity, and thus can be useful in producing viruses used for vaccines.

5 Claims, 6 Drawing Sheets

Day 6　　　　　　　　　　Day 41

Day 24　　　　　　　　　　Day 126

MDCK-DERIVED CELL STRAIN SUSPENSION-CULTURED IN PROTEIN-FREE MEDIUM AND METHOD FOR PROLIFERATING VIRUS USING CELL STRAIN

CROSS REFERENCE TO RELATED APPLICATIONS

This application is a National Stage of International Application No. PCT/KR2014/004949 filed Jun. 3, 2014, claiming priority based on Korean Patent Application No. 10-2013-0065229 filed Jun. 7, 2013, the contents of all of which are incorporated herein by reference in their entirety.

FIELD OF THE INVENTION

The present invention relates to a novel MDCK-derived cell line capable of being suspension-cultured in a protein-free medium and a method for proliferating viruses using such MDCK cell line to produce vaccines.

BACKGROUND OF THE INVENTION

In general, fertilized eggs are used for influenza vaccine production. However, using fertilized eggs has the following disadvantages: chickens suitable for the production should be bred and managed; the influenza vaccine production should be adjusted to the production range of the fertilized eggs; and egg proteins cannot be completely eliminated which renders the vaccine unsuitable for inoculation to a person allergic to the egg proteins. Since long time ago, studies have been conducted on influenza vaccines produced by using cell cultures in order to replace the fertilized eggs that have the above disadvantages. Using cell cultures allows mass production in a short time owing to the indefinite supply of animal cells used for the cell culture. In addition, it has advantages in that the vaccine can be inoculated to a person allergic to egg proteins; and the influenza vaccines which cannot be isolated from fertilized eggs can be isolated from the cells. Furthermore, the viruses proliferated in cells show less gene mutations of viral antigens than in fertilized eggs.

Madin Darby canine kidney (hereinafter referred to as "MDCK") cell lines, established from canine kidney, shows very strong surface adhesion; has been cultured using animal sera; and requires much space for mass production thereby necessitating high expenses. Also, adherent MDCK cell lines were reported to show high tumorigenicity.

Thus, there is a need to develop a novel MDCK cell line adapted to suspension cultures using a culture medium containing no animal-derived serum and proteins, which shows significantly lower tumorigenicity than conventional adherent MDCK.

SUMMARY OF THE INVENTION

Therefore, it is an object of the present invention to provide a novel MDCK-derived cell line capable of being suspension-cultured in a protein-free medium which has a low tumorigenicity while causing less viral antigenic variations, and thus can be useful in producing viruses used for vaccines.

It is another object of the present invention to provide a method for proliferating viruses using the MDCK-derived cell line to produce a vaccine.

In accordance with an object of the present invention, there is provided a Madin-Darby canine kidney (MDCK)-derived MDCKS-MG cell line capable of being suspension-cultured in a protein-free medium (Accession No. KCLRF-BP-00297).

In accordance with another object of the present invention, there is provided a method for proliferating a virus to produce a vaccine, which comprises the steps of:

1) infecting a MDCK-derived MDCKS-MG cell line (Accession No. KCLRF-BP-00297) with the virus;

2) culturing the MDCK-derived MDCKS-MG cell line infected with the virus; and 3) isolating the virus from the cell culture obtained in step 2).

The MDCK-derived cell line of the present invention is capable of being suspension-cultured in a protein-free medium without defect in cell growth; exhibits high and uniform productivity for various viruses, while causing less viral antigenic variations with low tumorigenicity; and thus can be useful in producing viruses used for vaccines.

BRIEF DESCRIPTION OF THE DRAWING

The above and other objects and features of the present invention will become apparent from the following descriptions of the invention, when taken in conjunction with the accompanying drawings.

DETAILED DESCRIPTION OF THE INVENTION

Figure 1:
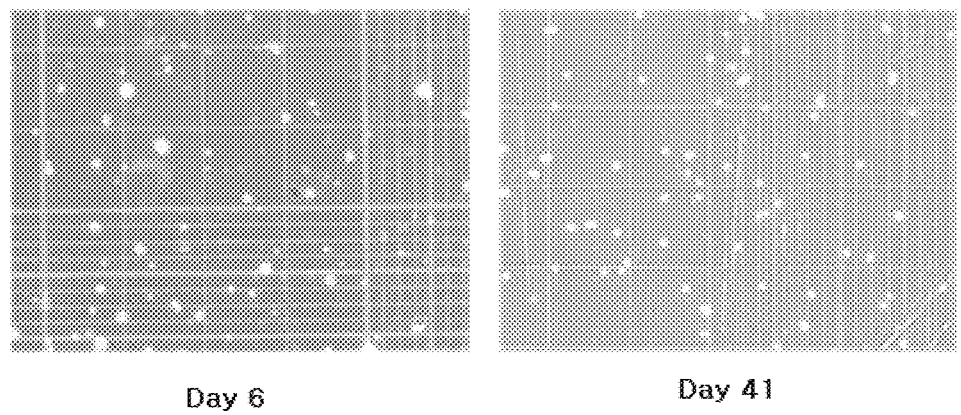
FIGS. 1 and 2 respectively show the cell state and growth curve of the candidate cell line A during suspension culture adaptation.

The present invention provides a MDCK-derived MDCKS-MG cell line capable of being suspension-cultured in a protein-free medium (Accession No. KCLRF-BP-00297, hereinafter also referred to as "candidate cell line B").

The MDCK-derived MDCKS-MG cell line of the present invention which is suspension-cultured in a protein-free medium containing no animal-derived substances has no defect in cell growth, exhibits low tumorigenicity, and shows high and uniform productivity for various viruses.

In addition, the MDCK-derived MDCKS-MG cell line of the present invention which is suspension-cultured in a protein-free ProCHO5 medium shows up to 128 times higher HA titer and up to $10^5$-fold superior PFU titer compared to other MDCK cell lines (e.g., candidate cell line A) which are suspension-cultured in EX-CELL MDCK medium, a commercial serum-free medium, indicating very excellent influenza virus productivity (Tables 5 to 9). Also, unlike candidate cell line A, the inventive cell line does not show mutations in the amino acid sequence of the viral HA-antigen after 3 culture passages (Table 11) and has relatively low tumorigenicity (Table 13). Further, the influenza vaccine produced from the cell line of the present invention shows excellent antibody-forming ability in mice (Table 14). Therefore it can be useful in producing viruses used for vaccines.

The present inventors named the MDCK-derived candidate cell line B as "MDCKS-MG", which was deposited at the Korea Cell Line Research Foundation with the Accession No. of KCLRF-BP-00297 on May 15, 2013.

In the present invention, "protein-free medium" refers to a serum-free medium containing no animal-derived serum, especially a culture medium containing no added protein with a molecular weight of 10 kDa or more at all. As an example, a protein-free medium of the present invention is preferably ProCHO5 medium which contains no added serum or protein at all.

The MDCK-derived MDCKS-MG cell line of the present invention can be produced, for example, according to a method comprising:

(a) thawing adherent MDCK cells (ATCC, CCL-34) followed by culturing them in a serum medium;

(b) culturing with passages the cells obtained in step a) in an adherent state; and (c) adapting the cells obtained in step b) to suspension-culture by way of lowering the serum content with each passage, replacing ProCHO4 medium (2% FBS) with ProCHO5 medium (serum-free), and stirring them at 120 to 130 rpm in 5% $CO_2$ incubator.

Hereinafter is explained specifically the method for producing MDCK-derived MDCKS-MG cell line of the present invention using the following steps.

Step (a)

First, information on the adherent MDCK cells used as parent cells is as follows:

Madin-Darby canine kidney (MDCK, ATCC) cells.

In step (a), after the MDCK parent cells (ATCC, CCL-34) are thawed, they are cultured in EMEM medium containing 10% fetal bovine serum (FBS) under the environment of 37° C. and 5% $CO_2$.

Step (b)

In step (b), after 3 to 4 days, the cells obtained in step (a) can be harvested by suspending them at the bottom of a flask using 0.25% trypsin EDTA. The cells can be cultured with passages in an adherent state with the ratio in cell amount of 1:4 to 1:50. The passage ratio can differ according to the cell growth rate, but preferably, it is 1:4 to 1:30.

Step (c)

In step (c), the cells obtained in step (b) are adapted to suspension-culture by lowering the serum content at each passage, replacing ProCHO4 medium (2% FBS) with ProCHO5 medium (serum-free), and stirring them at 120 to 130 rpm in 5% $CO_2$ incubator.

The cells are adapted to suspension-culture by lowering the serum content, for example, stirring them at 120 to 130 rpm in 5% $CO_2$ incubator: in ProCHO4 medium (2% FBS) on days 0-24, in ProCHO4 medium (1% FBS) on days 24-32, in a mixed medium of ProCHO4 and ProCHO5 (50:50, 1% FBS) on days 32-36, in a mixed medium of ProCHO4 and ProCHO5 (33:67, 0.5% FBS) on days 36-39, in a mixed medium of ProCHO4 and ProCHO5 (20:80) on days 39-42, and in ProCHO5 medium (protein-free) on day 42 or later.

The ProCHO5 medium can contain L-glutamine (Lonza), and commercialized products containing L-glutamine may include GlutaMax™ (invitrogen), GlutaminePlus™ (atlantabio), CellBoost™ (HyClone), RS-CHO™ (Sheffield), and the like.

The MDCK-derived MDCKS-MG cell line produced by the above method shows equal level of cell growth rate (FIG. 6) and high survival rate of about 97% or higher in each passage even when cultured with passages for a long time. In addition, it shows almost no differences between passages in the metabolism of substances such as glucose, lactate, glutamine and glutamate, or the virus-production ability. Thus, the MDCK-derived MDCKS-MG cell line of the present invention can be useful in proliferating viruses.

The present invention provides a method for proliferating viruses using the above MDCK-derived MDCKS-MG cell line. In addition, the present invention provides a virus produced by the above method, for example, an influenza virus produced by the above method. The viruses produced by the MDCKS-MG cell line of the present invention can be used for a vaccine, in viral infection diagnosis, or as antigens for antibody production or antibody-production assessment.

Therefore, the present invention provides a method for proliferating a virus to produce a vaccine using the above MDCK-derived MDCKS-MG cell line.

Specifically, the present invention provides a method for proliferating a virus, which comprises the steps of:

1) infecting a MDCK-derived MDCKS-MG cell line (Accession No. KCLRF-BP-00297) with the virus;

2) culturing the MDCK-derived MDCKS-MG cell line infected with the virus; and 3) isolating the virus from the cell culture thus obtained.

Accordingly, the present invention provides a vaccine produced by the above method.

The virus can be selected from a group consisting of an influenza virus, a Japanese encephalitis virus, a mumps virus, a rubella virus, a polio virus, herpes simplex virus type 1 (Herpes simplex virus-1, HSV-1), herpes virus type 2 (Herpes virus-2, HV-2), a measles virus, reovirus type 2 and type 3, a respiratory syncytial (RS) virus, a rabies virus, a yellow fever virus, adenovirus type 4, a Lassa virus, a vaccinia virus, a parvovirus, coxsackie virus type B3, B4 and B5, and a vesicular stomatitis virus, preferably, an influenza virus.

The influenza virus can be one which belongs to the Orthomyxovirus among the helical RNA viruses. It can be influenza virus type-A, type-B, or type-C, preferably, influenza virus type-A or type-B.

According to one embodiment of the present invention, the influenza virus can be H1N1 virus such as A/WS/33, IVR (Initiative for Vaccine Research)-116, IVR-148, IVR-145 or NYMC (New York Medical College) X-181; H3N2 virus such as A/Hongkong/8/68, NYMC X-161B, NYMC X-187, NYMC X-157 or IVR-147; or type-B virus such as B/Lee/40, B/Malaysia/2506/2004, B/Florida/4/2006 or B/Brisbane/60/2008.

In the above method for infecting a MDCK-derived MDCKS-MG cell line with a virus, the cell line can be infected by mixing them with an appropriate amount (e.g., 0.01 MOI) of a sterile viral solution. The condition for culturing the MDCK-derived MDCKS-MG cell line infected with the influenza virus is the same as for cell lines described above.

According to one embodiment of the present invention, the genetic stability of the viruses were compared by passaging influenza viruses in a MDCK-derived MDCKS-MG cell line and determining the amino acid sequences of HA and NA, major surface antigen of the passaged viruses. As a result, unlike the viruses passaged in the candidate cell line A, the amino acid sequences of HA and NA of the viruses passaged in the MDCK-derived MDCKS-MG cell line were found to be stable without gene mutations until passage 3 (Example 3).

In addition, influenza viruses were produced by infecting a MDCK-derived MDCKS-MG cell line with influenza viruses and culturing the cell line. The influenza viruses thus produced were purified to produce an influenza vaccine in an inactivated pulverized formulation. The produced vaccine was administered to 6-week-old female BALB/C mice and HI titer in the serum was analyzed. As a result, it was found that the antibody-forming ability was produced in the mice administered with the vaccine. Therefore, MDCK-derived MDCKS-MG cell line of the present invention is useful in the production of influenza viruses for a vaccine (Example 5).

EXAMPLES

Hereinafter, the present invention is explained specifically. The following Examples are intended to further illustrate the present invention without limiting its scope.

Example 1

Selection Process for Candidate Cell Lines 1.1. Thawing Adherent MDCK Cells

Frozen preserved adherent MDCK cells (obtained from: ATCC, CCL-34) were thawed and cultured in 15 mL of serum medium (EMEM medium supplemented with 10% FBS) (obtained from: Lonza). Cells stored in LN2 tank were put into 37° C. water bath and thawed. Resuspended cell solution was added to T75 flask containing serum medium, and then cultured in a 37° C. and 5% $CO_2$ incubator.

1.2. Adherent Culture

After 3-4 days, the cells obtained from 1.1 were cultured with passages at the ratio of 1:4 to 1:30. The mother cell was at passage 55. The subcultures were carried out by the following procedure.

T75 flask was taken out from the incubator of 1.1, removed of the medium, and washed. Cells were detached by treating with 0.25% trypsin-EDTA, and resuspended by pipetting with serum medium to a desired ratio. Subcultures were performed every 3-4 days at the passage ratios of 1:4 to 1:30.

Adherent culture was performed before the suspension adaptation.

1.3. Suspension Adaptation

The adherent cells obtained from 1.2 were adapted to suspension culture using 6 kinds of commercial serum-free medium such as EX-CELL™ MDCK 1.2 (Sigma), UltraMDCK™ (Lonza), and VP-SFM™ (Invitrogen) and so on. Among them, 2 kinds of medium were found to be suitable for the suspension culture, and 10 or more kinds of various cell lines were obtained from them. 2 kinds of candidate MDCK cell lines (candidate cell lines A and B) most suitable for the suspension culture were selected. Specific suspension adaptation procedures of candidate cell lines A and B are as follows.

1.3.1. Process for Suspension Adaptation of the Candidate Cell Line A

According to the processes described in 1.1 and 1.2, frozen preserved adherent MDCK cells (obtained from: ATCC, CCL-34) were thawed and cultured in an adherent state for 3 passages. Then, after resuspension in EX-CELL™ MDCK medium (Sigma, containing 6 mM L-glutamine) supplemented with 5% FBS at the concentration of 5e+05 cells/mL, the cells were put into 125 mL Erlenmeyer flask, stirred in an incubator at 120-130 rpm, and suspension-cultured in the orbital shaker (working volume (hereinafter, "W.V."): 10 mL, initial cell inoculation concentration: 5e+05 cells/mL, p80).

The initial cell inoculation concentration was adjusted every 3-4 days to be 5e+05 cells/mL or higher, and the FBS concentration was reduced at each passage starting from 5%. The summary table of the mixtures for suspension culture adaptation of candidate cell line A is shown in Table 1 below.

TABLE 1

| Period (day) | FBS concentration (%) |
|---|---|
| 0-3 | 5 |
| 3-6 | 2.5 |
| 6-9 | 1 |
| 9-13 | 0.5 |
| 13 or later | 0 (Serum-free) |

The progress for suspension culture adaptation of the candidate cell line A is as follows:

On day 13, cell growth began to take place, and from day 15, the cell state was improved with the survival rate of 90% or higher. On day 23, 4-fold or higher number of cells were attained for 3 times consecutively with the survival rate of 90% or higher. On day 30, the cell growth became 4-fold or higher and the cell line having the survival rate of 97% was obtained. Then the suspension culture adaptation of candidate cell line A was completed.

Figure 2:
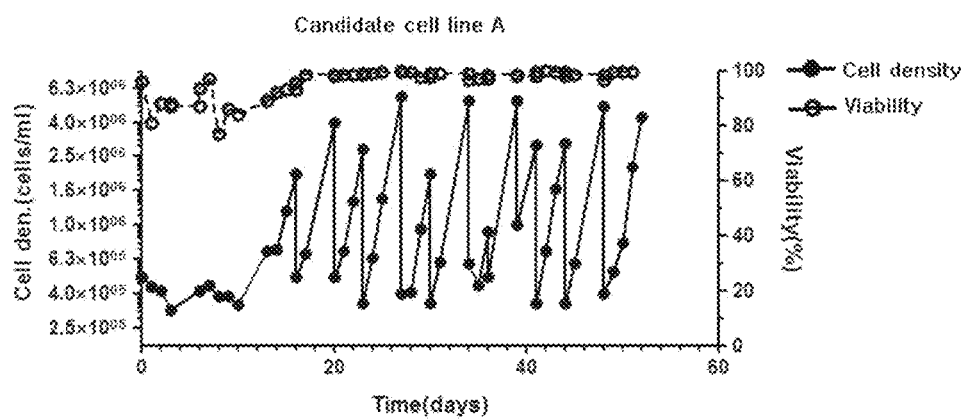

Cell state on days 6 and 41 of the suspension culture adaptation of candidate cell line A is shown in FIG. 1, and growth curve (cell density and survival rate) of the candidate cell line A was shown in FIG. 2.

As shown in FIG. 1, the cell state on day 6 revealed swelling and aggregation with many dead cells, while the cell state on day 41 revealed almost equally sized cell shapes and high survival rates.

1.3.2. Suspension Adaptation Process of the Candidate Cell Line B

According to the processes described in the 1.1 and 1.2, frozen preserved adherent MDCK cells (obtained from: ATCC, CCL-34) were thawed and cultured in an adherent state for 3 passages. Then, after resuspension in ProCHO4 medium (Lonza, containing 4 mM L-glutamine) supplemented with 2% FBS at the concentration of 5e+05 cells/mL, the cells were put into 500 mL Erlenmeyer flask, stirred in an incubator at 120-130 rpm, and cultured in the orbital shaker (W.V.: 130 mL, initial cell inoculation concentration: 7e+05 cells/mL, p76).

The initial cell inoculation concentration was adjusted every 3-4 days to be 5e+05 cells/mL or higher, and the FBS concentration was reduced at each passage starting from 2%. The summary table of the mixtures for suspension culture adaptation of candidate cell line B is shown in Table 2 below.

TABLE 2

| Period (day) | ProCHO4 (%) | ProCHO5 (%) | FBS Concentration (%) |
|---|---|---|---|
| 0-24 | 100 | 0 | 2 |
| 24-32 | 100 | 0 | 1 |
| 32-36 | 50 | 50 | 1 |
| 36-39 | 33 | 67 | 0.5 |
| 39-42 | 20 | 80 | 0 (serum-free) |
| 42 or later | 0 | 100 | 0 |

The progress for suspension culture adaptation of the candidate cell line B is as follows:

On day 21, cell growth began to take place, and cell state was improved with the survival rate of 90% or higher. On day 24, after 2 times of doubling, FBS concentration was reduced to 1%. While adapting the cells to the medium replacement from ProCHO4 to ProCHO5, ProCHO4 (containing 2% FBS) was replaced with ProCHO5 (serum-free medium, Lonza, Cat#12-766Q) on day 32. Until day 56, the cells were subcultured with the W.V. reduced every 3-4 days due to the decline of cell growth, in which period the survival rate declined to the range between 30 and 40%. After day 59, cell growth slowly began to take place, and the survival rate was also recovered to about 80%. On day 95, the cell growth was observed to be in a stable state with cell doublings, showing the survival rate of 90% or higher. On day 99, cells showed 4-fold or higher cell growth, and cell line having the survival rate of 99% (W.V. 200 mL or higher) was obtained.

Figure 3:
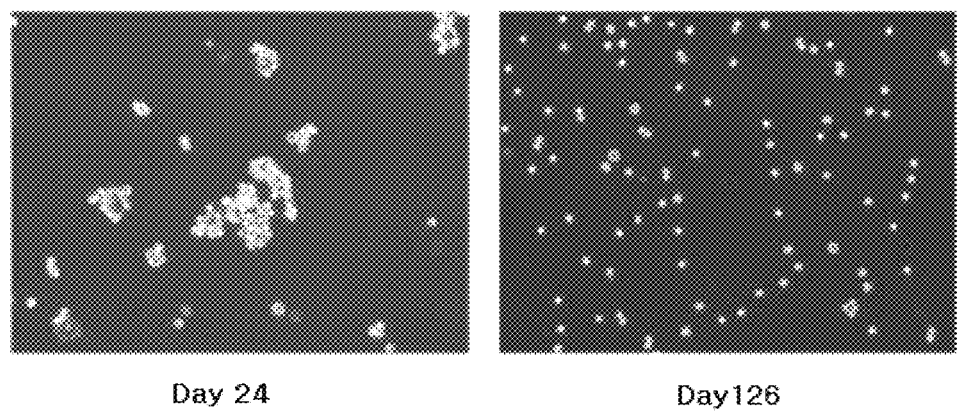
FIGS. 3 and 4 respectively show the cell state and growth curve of the candidate cell line B during suspension culture adaptation.
Figure 4:
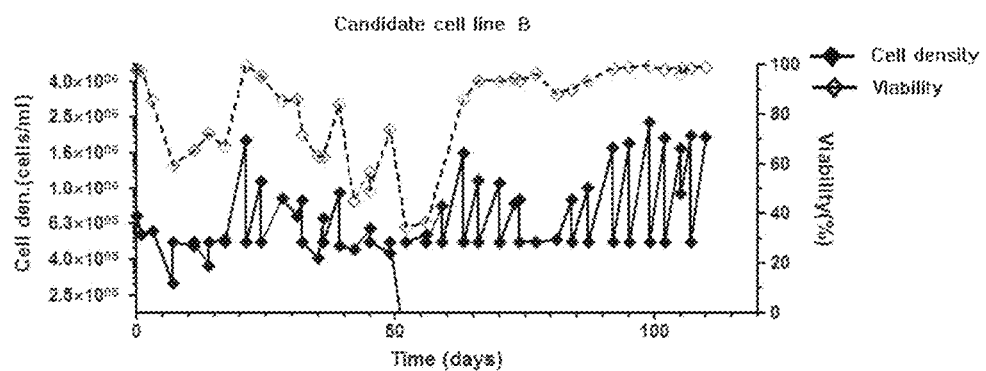

Cell state on days 24 and 126 of the suspension culture adaptation of candidate cell line B is shown in FIG. 3, and growth curve (cell density and survival rate) of the candidate cell line B are shown in FIG. 4. As shown in FIG. 3, the cell state on day 24 revealed much aggregation with some dead cells, while the cell state on day 126 revealed almost equally sized cell shapes and high survival rates.

Example 2

Comparative Analysis of Candidate Cell Line and Selection of the Production Cell Line 2.1. Comparison of Cell Line Stability Through Long-Term Subcultures 2.1.1. Candidate Cell Line A To determine the cell growth of candidate cell line A at each passage, the cell line A was subcultured by way of centrifuging the cells and removing the culture medium followed by putting a new medium, to adjust the number of cells to be 5e+05 cells/mL, once every 3-4 days for 100 days. The result of subcultures of candidate cell line A is shown in FIG. 5.

Figure 5:
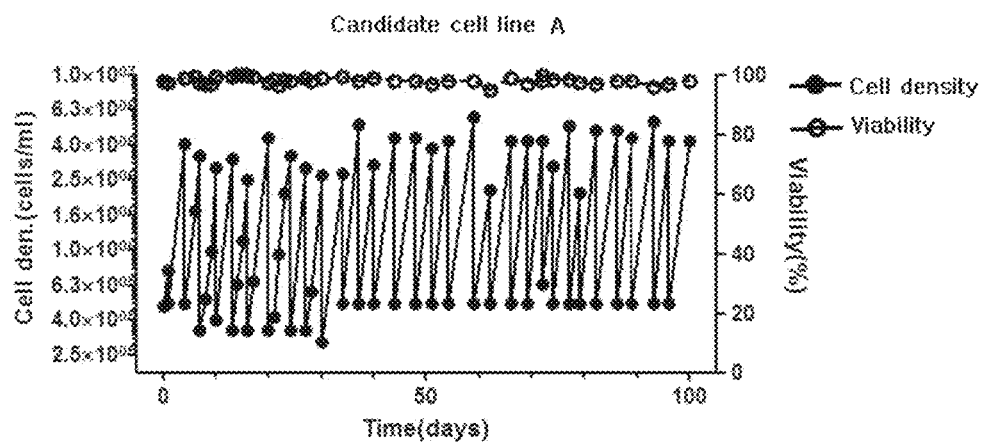
FIGS. 5 and 6 show the results of subcultures of the candidate cell lines A and B, respectively.

As shown in FIG. 5, even in the long-term cultures with 35 passages or more (p85+35: 85 passages before the suspension-culture, and 35 passages after the suspension), the candidate cell line A showed almost equal level of cell growth at each passage.

2.1.2. Candidate Cell Line B

To determine the cell growth of candidate cell line B at each passage which completed the suspension-culture adaptation in Example 1, the cell line B was subcultured by way of centrifuging the cells and removing the culture medium followed by putting a new medium, to adjust the number of cells to be 5e+05 cells/mL, once every 3-4 days for 274 days. The result of subcultures of candidate cell line B is shown in FIG. 6.

Figure 6:
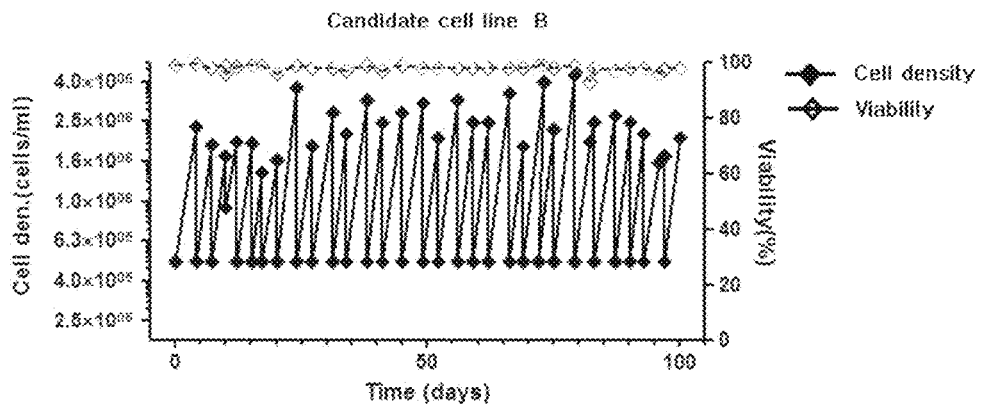

As shown in FIG. 6, even in the long-term cultures with 51 passages or more (p85+51: 85 passages before the suspension-culture, and 51 passages after the suspension), the candidate cell line B showed almost equal level of cell growth at each passage until passage 45 (p89+45).

2.2. Comparison of the Doubling Time and Maximum Viable Cell Density Between Passages Using the cell density and cell survival rate of candidate cell lines A and B, doubling time ($T_d$) was measured and maximum viable cell density determined.

Herein, $T_d$ was calculated according to the formula below in log phase based on the number of cells measured every day, and maximum viable cell density ($VCD_{max}$) was represented by the maximum value of the number of cells measured everyday, which showed its peak between 4-7 days. Cell survival rate was measured using a hemocytometer.

$$\mu = \frac{1}{x} \times \frac{dt}{dx'} \qquad \text{[Formula]}$$
$$T_d = \frac{\ln 2}{\mu \max}$$

wherein,
μ is a specific growth rate;
x is a number of cells;
dt is an amount of change in time;
dx' is an amount of change in the number of cells;
ln2 is a value in which the number of cells doubles; and
μmax is a maximum of specific growth rate.

In candidate cell line A, between the passages of p85+7 to p85+45, Td and maximum viable cell density were in the same level; in average, Td was about 28 hr, maximum viable cell density was 5.28±0.79e+06 cells/mL, and cell survival rate was 97% or higher.

In candidate cell line B, between the passages of p 89+2 to p89+33, Td and maximum viable cell density were in the same level; in average, Td was about 38 hr, maximum viable cell density was 2.60±0.62e+06 cells/mL, and cell survival rate was 97% or higher.

TABLE 3

| | Passage | $T_d$ (h) | $VCD_{max}$/AVG (cells/mL) | Survival rate (%) |
|---|---|---|---|---|
| Candidate cell line A | P85 + 7~45 | 28.2 ± 2.4 | 5.28 ± 0.79e+06 | 97 ± 1.9 |
| Candidate cell line B | P89 + 2~33 | 37.9 ± 6.1 | 2.60 ± 0.62e+06 | 97 ± 1.3 |

2.3. Comparison of the Productivity of Influenza Virus of Candidate Cell Lines

Using candidate cell lines A and B, 11 types of influenza viruses, such as H1N1 virus (A/WS/33, IVR-116, IVR-148, and IVR-145), H3N2 virus (A/Hongkong/8/68, NYMC X-161B, NYMC X-157, and IVR-147), and B virus (B/Lee/40, B/Malaysia/2506/2004, and B/Brisbane/60/2008) were proliferated.

To infect the candidate cell lines A and B with the influenza viruses, EX-CELL MDCK medium (sigma) and ProCH05 medium (obtained from: Lonza) were each added with 0.01 MOI and 10 ug/mL TPCK-trypsin, and suspension-cultured with shaking at 33-37° C. at the presence of 5% $CO_2$. For 7 days therefrom, 1 mL of each sample was collected using a pipette every day, and the productivity of candidate cell lines A and B was assessed through HA assay (Heamagglutination assay) and PFU (Plaque-forming unit).

The HA titer and PFU titer were measured according to the method disclosed in the document [Manual for the laboratory diagnosis and virological surveillance of influenza, WHO].

Figure 7:
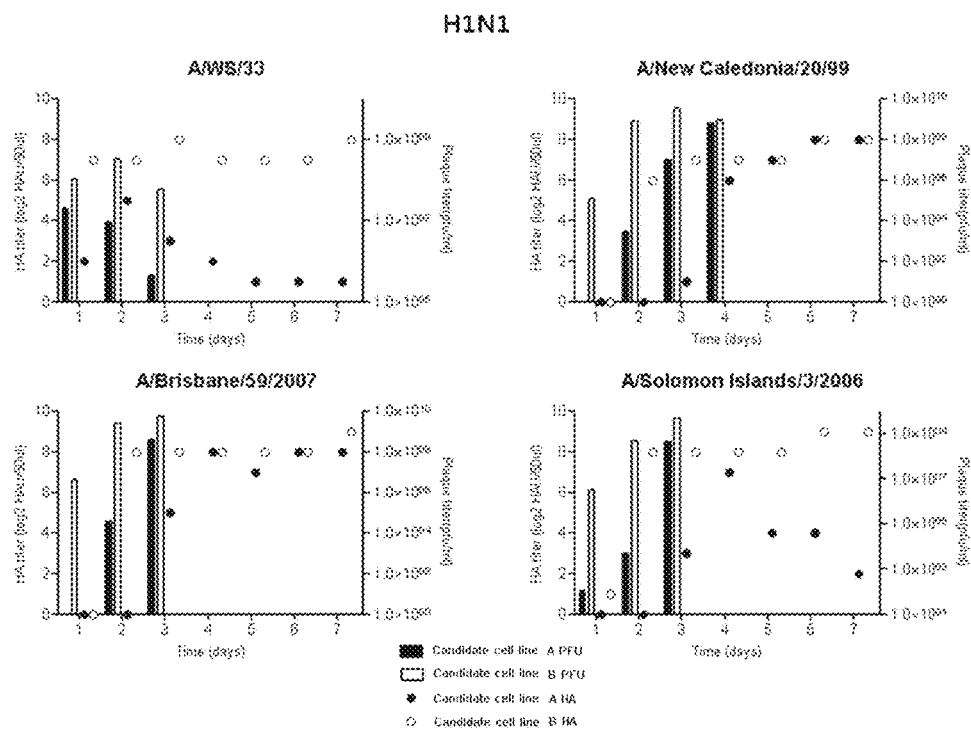
FIGS. 7 to 9 show the analysis results of the productivity of influenza viruses of H1N1, H3N2 and B types in the candidate cell lines A and B, respectively.
Figure 8:
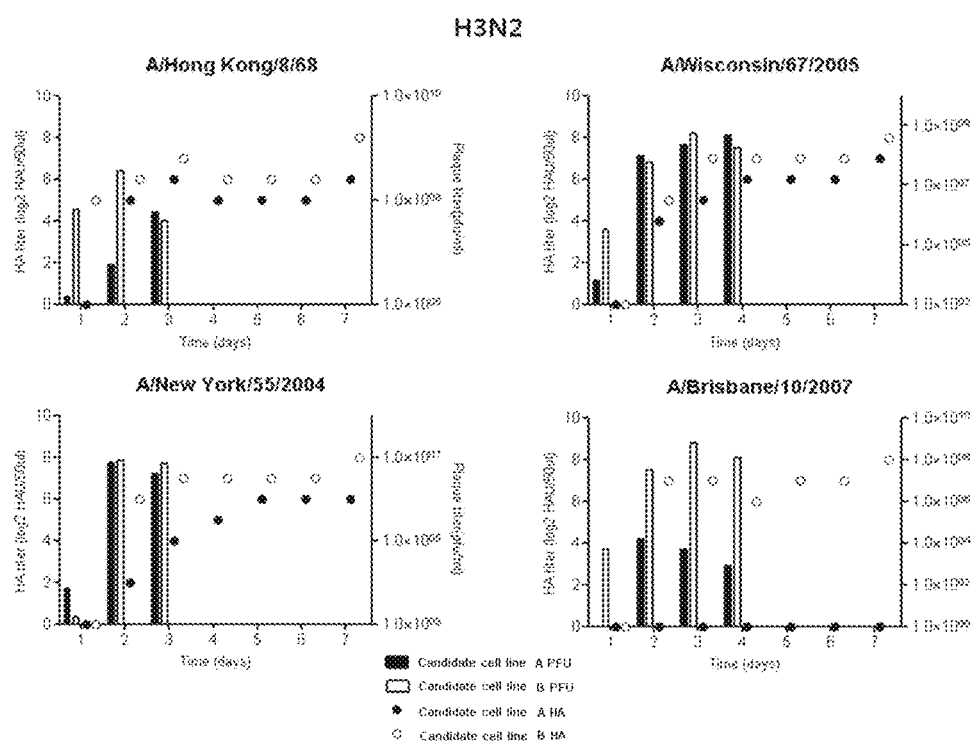
Figure 9:
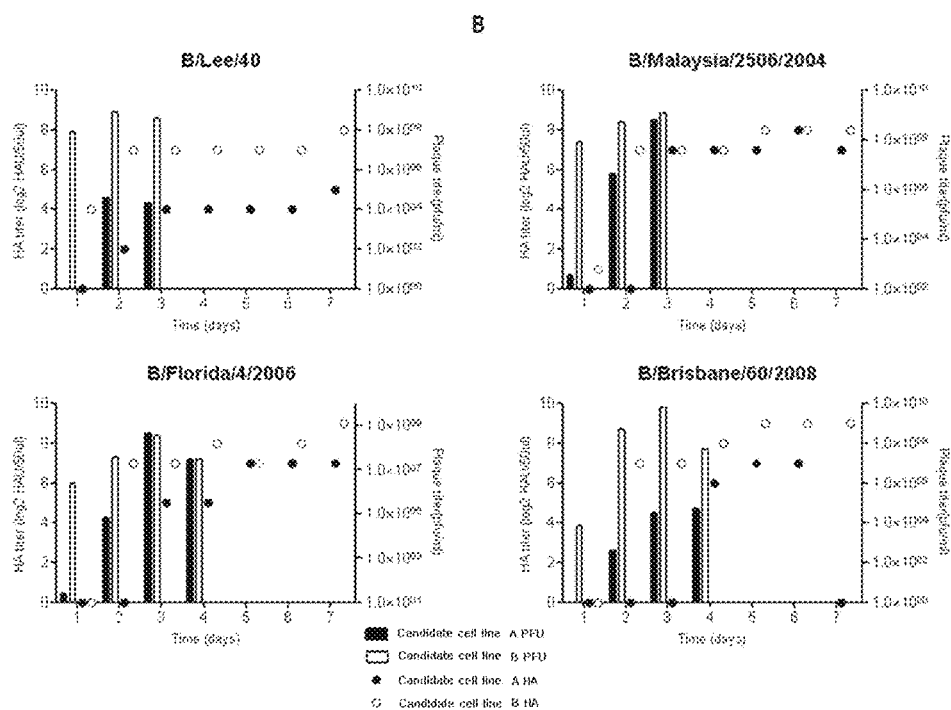

As a result, 4 types of H1N1 viruses and 4 types of H3N2 viruses in candidate cell line B showed higher titer more rapidly as compared to candidate cell line A (FIGS. 7 and 8). It should be noted that IVR-147 didn't show any HA titer in candidate cell line A (FIG. 8). Also, 4 types of B viruses in candidate cell line B showed higher titer more rapidly as compared to cell line A (FIG. 9).

Meanwhile, the HA titer in candidate cell line B represented as a ratio relative to that of 11 types of influenza viruses in candidate cell line A (i.e., setting the HA titer of 11 types of influenza viruses in candidate cell line A to 1) was shown in Tables 4 to 6. As a result, the level of productivity in candidate cell line B was the same or higher as compared to candidate cell line A, and especially, the productivity of IVR-147 virus was found to be 128 times higher.

TABLE 4

| HA titer | H1N1 virus | | | |
|---|---|---|---|---|
| strain | A/WS/33 | A/New Caledonia/20/99 | A/Brisbane/59/2007 | A/Solomon Islands/3/2006 |
| Reassortant | — | IVR-116 | IVR-148 | IVR-145 |
| Candidate cell line A | 1.0 | 1.0 | 1.0 | 1.0 |
| Candidate cell line B | 4.0 | 1.0 | 1.0 | 2.0 |

TABLE 5

| HA titer | H3N2 virus | | | |
|---|---|---|---|---|
| strain | A/Hong Kong/8/68 | A/Wisconsin/67/2005 | A/New York/55/2004 | A/Brisbane/10/2007 |
| Reassortant | — | NYMC X-161B | NYMC X-157 | IVR-147 |
| Candidate cell line A | 1.0 | 1.0 | 1.0 | 1.0 |
| Candidate cell line B | 1.0 | 2.0 | 2.0 | 128.0 |

TABLE 6

| HA titer | B virus | | |
|---|---|---|---|
| strain | B/Lee/40 | B/Malaysia/2506/2004 | B/Brisbane/60/2008 |
| Candidate cell line A | 1.0 | 1.0 | 1.0 |
| Candidate cell line B | 8.0 | 2.0 | 4.0 |

Also, the PFU titer of candidate cell line B represented as a ratio relative to that of 11 types of influenza viruses in candidate cell line A (i.e., setting the PFU titer of 11 types of influenza viruses in candidate cell line A to 1) was shown in Tables 7 to 9. As a result, the level of productivity of 11 types of viruses in candidate cell line B was the same or higher as compared to candidate cell line A, and especially, the productivity of B/Brisbane/60/2008IVR-1 virus was found to be $10^5$ times higher at maximum.

TABLE 7

| PFU titer | H1N1 virus | | | |
|---|---|---|---|---|
| strain | A/WS/33 | A/New Caledonia/20/99 | A/Brisbane/59/2007 | A/Solomon Islands/3/2006 |
| Reassortant | — | IVR-116 | IVR-148 | IVR-145 |
| Candidate cell line A | 1.0 | 1.0 | 1.0 | 1.0 |

TABLE 7-continued

| PFU titer | H1N1 virus | | | |
|---|---|---|---|---|
| Candidate cell line A | 17.2 | 5.8 | 6.9 | 11.1 |

TABLE 8

| PFU titer | H3N2 virus | | | |
|---|---|---|---|---|
| strain | A/Hong Kong/8/68 | A/Wisconsin/67/2005 | A/New York/55/2004 | A/Brisbane/10/2007 |
| Reassortant | — | NYMC X-161B | NYMC X-157 | IVR-147 |
| Candidate cell line A | 1.0 | 1.0 | 1.0 | 1.0 |
| Candidate cell line B | 5.9 | 1.2 | 1.2 | 39333.0 |

TABLE 9

| PFU titer | B virus | | |
|---|---|---|---|
| strain | B/Lee/40 | B/Malaysia/2506/2004 | B/Brisbane/60/2008 |
| Candidate cell line A | 1.0 | 1.0 | 1.0 |
| Candidate cell line B | 19864.9 | 2.0 | 125250.0 |

2.4. Comparison of the Productivity of Influenza Virus in Candidate Cell Line B and Adherent MDCK Using candidate cell line B, and adherent MDCK which employs the serum-containing medium, 9 types of influenza viruses, such as H1N1 virus (IVR-116, IVR-148, and IVR-145), H3N2 virus (NYMC X-161B, NYMC X-157, and IVR-147), and B virus (B/Malaysia/2506/2004, B/Florida/4/2006, and B/Brisbane/60/2008) were proliferated.

To infect the candidate cell line B and adherent MDCK with the influenza viruses, ProCHO5™ medium (Obtained from: Lonza) and EMEM (Lonza) containing 10% bovine serum were each added with 0.01 MOI of the virus and 10 μg/mL of TPCK-trypsin. The candidate cell line B to be suspension-cultured at the presence of 5% $CO_2$ was suspension-cultured at 33-37° C. with shaking; whereas the adherent MDCK was cultured without shaking but otherwise in the same condition as above. On Days 2 and 3 from the culture, 1 mL of each sample was collected using a pipette, and the productivity of candidate cell lines B and the adherent MDCK was assessed through HA assay and PFU.

The HA and PFU titers were measured according to the method disclosed in the document [Manual for the laboratory diagnosis and virological surveillance of influenza, WHO]. The highest titer during Days 2 and 3 was regarded as a maximum titer, which was used for comparison.

As a result, 3 types of H1N1 viruses with candidate cell line B showed the same or maximum 2 times higher HA titers. The levels of PFU were also shown to be twice higher or 0.3 times lower, but the differences were within the range of experimental errors, and therefore they were determined to be similar levels. And, 3 types of H3N2 viruses in candidate cell line B showed 8 times higher HA titer than in the adherent MDCK, and PFU titer was shown to be at least 100 times higher. Especially, B type B/Brisbane/60/2008 showed $10^7$ times higher PFU titer in candidate cell line B (Table 10).

TABLE 10

| HA titer | H1N1 virus | | |
|---|---|---|---|
| strain | A/New Caledonia/20/99 | A/Brisbane/59/2007 | A/Solomon Islands/3/2006 |
| Reassortant | IVR-116 | IVR-148 | IVR-145 |
| Adherent MDCK | 1.0 | 1.0 | 1.0 |
| Candidate cell line B | 1.0 | 2.0 | 2.0 |
| HA titer | H3N2 virus | | |
| strain | A/Wisconsin/67/2005 | A/New York/55/2004 | A/Brisbane/10/2007 |
| Reassortant | NYMC X-161B | NYMC X-157 | IVR-147 |
| Adherent MDCK | 1.0 | 1.0 | 1.0 |
| Candidate cell line B | 16.0 | 8.0 | 16.0 |
| HA titer | B virus | | |
| strain | B/Malaysia/2506/2004 | B/Florida/4/2006 | B/Brisbane/60/2008 |
| Adherent MDCK | 1.0 | 1.0 | 1.0 |
| Candidate cell line B | 2.0 | 16.0 | 4.0 |
| PFU titer | H1N1 virus | | |
| strain | A/New Caledonia/20/99 | A/Brisbane/59/2007 | A/Solomon Islands/3/2006 |
| Reassortant | IVR-116 | IVR-148 | IVR-145 |
| Adherent MDCK | 1.0 | 1.0 | 1.0 |
| Candidate cell line B | 0.7 | 2.1 | 0.7 |
| PFU titer | H3N2 virus | | |
| strain | A/Wisconsin/67/2005 | A/New York/55/2004 | A/Brisbane/10/2007 |
| Reassortant | NYMC X-161B | NYMC X-157 | IVR-147 |
| Adherent MDCK | 1.0 | 1.0 | 1.0 |
| Candidate cell line B | 956.1 | 102.1 | 831.0 |
| PFU titer | B virus | | |
| strain | B/Malaysia/2506/2004 | B/Florida/4/2006 | B/Brisbane/60/2008 |
| Adherent MDCK | 1.0 | 1.0 | 1.0 |
| Candidate cell line B | 6.2 | 10806.5 | 17892857.1 |

2.5. Selection of the Production Cell Line

Based on the results as above, cell line B was selected as the production cell line of the present invention and was named "MDCKS-MG", which was deposited at the Korea Cell Line Research Foundation on May 15, 2013 with the Accession No. of KCLRF-BP-00297.

Example 3

Comparison of the Genetic Stability of the Viruses

Influenza viruses proliferate according to a changed gene sequence if changes in genetic information take place during proliferation in a host; such mutated portion can be a major surface antigen such as HA or NA antigen. As a result, the antibodies induced by the changed surface antigen may not exhibit vaccine effects as expected.

Therefore, the viruses passaged in the candidate cell line A and MDCKS-MG cell line were examined for any changes in the amino acid sequences of major surface antigens HA and NA; and the effect on the antibody formation was examined for any changes.

Specifically, taking refererence to the basic gene sequence ("Ref.") registered at NCBI, the gene sequences of influenza viruses produced in the cell line A and MDCKS-MG cell line were compared with the influenza viruses produced in the fertilized egg.

First, the virus derived from the fertilized egg was obtained from the NIBSC; and the amino acid sequences of HA and NA antigens were examined. The candidate cell line A and MDCKS-MG cell line were infected for 3 passages with H1N1 virus (IVR-116, IVR-148, IVR-145, and NYMC X-181), H3N2 virus (NYMC X161B, NYMC X-157, IVR-147, and NYMC X-187), and B virus (B/Malaysia/2506/2004, and B/Brisbane/60/2008). Then, examination was conducted for any changes in the amino acid sequences of HA and NA antigens in the influenza viruses obtained from passages 1 and 3 of the candidate cell line A and MDCKS-MG cell line. The comparison results of HA and NA amino acid sequences are shown in Table 11 and 12, respectively.

The amino acid sequence analysis was referred to the Cosmo genetech Co. where the changed amino acid (a.a) as compared to the standard virus amino acid, and its site (a.a site) were determined. The viruses derived from the fertilized egg were shown in the column for "Egg".

As shown in Table 11 below, it was found that the HA amino acid sequences of the passaged viruses in cell line A up to passage 3 had changes in 3 types of line (IVR-116, IVR-145, and NYMC X-181). However, MDCKS-MG cell line didn't show any changes in amino acids.

Also, as shown in Table 12, the NA amino acid sequences didn't contain any mutated amino acid, and there were no significant changes in amino acid sequence between viruses derived from the candidate cell line A and MDCKS-MG cell line and those from the fertilized egg. As such, the MDCKS-MG cell line was found to have no significant gene mutations up to passage 3 during the virus proliferation.

TABLE 11

| | strains | a.a site | Ref. | Egg | Candidate cell line A P1 | Candidate cell line A P3 | MDCKS-MG cell line P1 | MDCKS-MG cell line P3 |
|---|---|---|---|---|---|---|---|---|
| H1N1 | A/New Caledonia/20/99 (IVR-116) | 150 | A | A | A | E | A | A |
| | A/Brisbane/59/2007 (IVR-148) | no mutation | — | — | — | — | — | — |
| | A/Solomon Islands/3/2006 (IVR-145) | 456 | S | S | S | F | S | S |
| | | 540 | R | L | L | L | L | L |
| | A/California/7/2009 (NYMC X-181) | 240 | R | R | Q | Q | R | R |

TABLE 11-continued

| strains | | a.a site | Ref. | Egg | Candidate cell line A P1 | Candidate cell line A P3 | MDCKS-MG cell line P1 | MDCKS-MG cell line P3 |
|---|---|---|---|---|---|---|---|---|
| H3N2 | A/Wisconsin/67/2005 (NYMC X-161B) | no mutation | — | — | — | — | — | — |
| | A/New York/55/2004 (NYMC X-157) | 219 | T | A | A | A | A | A |
| | | 524 | K | E | E | E | E | E |
| | A/Brisbane/10/2007 (IVR-147) | 210 | L | P | P | P | P | P |
| | | 213 | Q | K | K | K | K | K |
| | | 505 | D | N | N | N | N | N |
| | A/Victoria/210/2009 (NYMC X-187) | no mutation | — | — | — | — | — | — |
| B | B/Malaysia/2506/2004 | no mutation | — | — | — | — | — | — |
| | B/Brisbane/60/2008 | 212 | N | S | S | S | S | S |

TABLE 12

| strains | | a.a site | Ref. | Egg | Candidate cell line A P1 | Candidate cell line A P3 | MDCKS-MG cell line P1 | MDCKS-MG cell line P3 |
|---|---|---|---|---|---|---|---|---|
| H1N1 | A/New Caledonia/20/99 (IVR-116) | no mutation | — | — | — | — | — | — |
| | A/Brisbane/59/2007 (IVR-148) | no mutation | — | — | — | — | — | — |
| | A/Solomon Islands/3/2006 (IVR-145) | 157 | T | A | A | A | A | A |
| | A/California/7/2009 (NYMC X-181) | no mutation | — | — | — | — | — | — |
| H3N2 | A/Wisconsin/67/2005 (NYMC X-161B) | no mutation | — | — | — | — | — | — |
| | A/New York/55/2004 (NYMC X-157) | no mutation | — | — | — | — | — | — |
| | A/Brisbane/10/2007 (IVR-147) | no mutation | — | — | — | — | — | — |
| | A/Victoria/210/2009 (NYMC X-187) | no mutation | — | — | — | — | — | — |
| B | B/Malaysia/2506/2004 | no mutation | — | — | — | — | — | — |
| | B/Brisbane/60/2008 | no mutation | — | — | — | — | — | — |

Example 4

Comparison of Tumorigenecity (Mouse-in House Tumorigenesis)

MDCK cells are known to have tumorigenicity when cultured as adherent cells and the tumorigenicity tends to increase when suspension-cultured. Tumorigenicity can be assessed by administering the cells themselves to a highly sensitive nude mouse. To use animal cells such as MDCK cells in producing biological products, their safety must be fully verified. To be used as production cells, it is preferable that the cells have low or no tumorigenicity.

To compare the tumorigenicity of cell line A and MDCKS-MG cell line, experiments were conducted as follows. Cell line A or MDCKS-MG cell line was injected to 10 nude mice per group hypodermically at the concentration of $10^3$ cells/mL (1.00e+03), $10^5$ cells/mL (1.00e+05) or $10^7$ cells/mL (1.00e+07), and tumor formation was observed for 11 weeks. The tumor formation was determined to be positive when the size of tumor became 100 mm$^3$ or bigger. The negative control group was injected with PBS and positive control group was implanted with Hela cell (ATCC) at the concentration of $10^7$ cells/mL, and the tumor formation was observed. The results of number of mice exhibiting tumor formation are shown in Table 13.

As shown in Table 13, cell line A-injected group showed tumor formation in 2 mice at $10^5$ cells/mL, and 9 mice at $10^7$ cells/mL; and positive control group (Hela cell) also showed tumor formation in 9 mice. However, the MDCKS-MG cell line-injected group showed tumor formation in only 1 mouse at $10^7$ cells/mL Therefore, it was found that the tumorigenicity of MDCKS-MG cell line was significantly lower than cell line A.

TABLE 13

| | Number of cells administrated | Number of mice with tumor formation |
|---|---|---|
| PBS | — | 0/10 |
| Hela Cell | 1.00e+07 | 9/10 |
| Candidate cell line A | 1.00e+03 | 0/10 |
| | 1.00e+05 | 2/10 |
| | 1.00e+07 | 9/10 |
| MDCKS-MG cell line | 1.00e+03 | 0/10 |
| | 1.00e+05 | 0/10 |
| | 1.00e+07 | 1/10 |

Example 5

Immunogenicity Confirmation (Mouse-in House Study)

The most important role of a vaccine is the antibody-forming ability to afford immunity. The typical method to confirm the antibody production against the influenza virus is a biological assay called HI assay. Therefore, to confirm the antibody-forming ability of the influenza viruses grown in MDCKS-MG cell line, the following procedure was performed.

In the same way as described in Example 2, the three types of influenza viruses of the present invention grown in MDCKS-MG cell line, A/California/7/2009 (NYMC X-181), A/Victoria/210/2009 (NYMC X-187) and B/Brisbane/60/2008 (yamagata lineage), were centrifuged using a ultrahigh speed centrifuge. In order to obtain more pure viruses, sucrose was added with differing concentration gradients of 20%, 25%, and 30%; and was isolated the virus layer only. After removing sucrose by dialysis, the viruses were pulverized using Triton X-100, and finally filtered through a sterilization filter to obtain the virus vaccines.

On the other hand, 6-week-old female BALB/C mice thus obtained were assigned to each group at eight mice per group, and 3 µg, 1 µg and 1 µg of virus vaccine were administered by intramuscular injection to the groups, respectively. The vaccines were administered twice with 2 weeks of interval. HI analysis was conducted using the mouse serum 7 weeks after the first vaccination. The serum was obtained by sampling blood from the ophthalmic vein using a syringe, followed by centrifugation at 6,000 rpm for 10 min.

HI assay was conducted in the same manner as Example 2 in accordance with the disclosed method in the literature [Manual for the laboratory diagnosis and virological surveillance of influenza]. The ratio of the number of the mice with HI titers of 40 or higher to the total number of mice; the Geometric Mean Titre (GMT); and the range of HI titers within a group are shown in Table 14 below.

As shown in Table 14, in the group where 1 µg or more of the virus vaccine was administered, the ratio (%) of the mice with HI titer of 40 or higher among the total mice in a group was 70% or higher, addressing that the vaccine of the present invention has antibody-forming ability.

Thus, the antigen produced in MDCKS-MG cell line of the present invention has excellent antibody-forming ability, and can be used for the production of influenza viruses for a vaccine.

TABLE 14

| Virus | Measured value | Amount of antigen administered (µg) | | |
|---|---|---|---|---|
| | | 3 | 1 | 0.1 |
| H1N1 | Number of mice with 40 or higher HI titer/Number of total mice | 8/8 | 8/8 | 2/8 |
| | GMT | 160 | 207 | 20 |
| | HI titer range in a group | 80-320 | 80-640 | 10-80 |
| H3N2 | Number of mice with 40 or higher HI titer/Number of total mice | 7/8 | 8/8 | 7/8 |
| | GMT | 103 | 226 | 95 |
| | HI titer range in a group | 20-320 | 160-320 | 20-320 |

TABLE 14-continued

| Virus | Measured value | Amount of antigen administered (µg) | | |
|---|---|---|---|---|
| | | 3 | 1 | 0.1 |
| B | Number of mice with 40 or higher HI titer/Number of total mice | 8/8 | 8/8 | 6/8 |
| | GMT | 73 | 47 | 40 |
| | HI titer range in a group | 40-160 | 40-80 | 10-80 |

While the present invention has been described with respect to the above specific embodiments, it should be recognized that various modifications and changes may be made to the present invention by those skilled in the art which also fall within the scope of the present invention as defined by the appended claims.

What is claimed is:

1. A Madin-Darby canine kidney (MDCK)-derived MDCKS-MG cell line (Accession No. KCLRF-BP-00297), which is suspension-cultured in a protein-free medium, wherein the protein-free medium contains serum in a concentration of 2% initially and then the concentration of serum decreases to 0% gradually.

2. The MDCK-derived MDCKS-MG cell line of claim 1, wherein the cell line proliferates a virus.

3. The MDCK-derived MDCKS-MG cell line of claim 2, wherein the virus is selected from the group consisting of:
   an influenza virus, a Japanese encephalitis virus, a mumps virus, a rubella virus, a polio virus, herpes simplex virus type 1 (Herpes simplex virus-1, HSV-1), herpes virus type 2 (Herpes virus-2, HV-2), a measles virus, reovirus type 2 and type 3, a respiratory syncytial (RS) virus, a rabies virus, a yellow fever virus, adenovirus type 4, a Lassa virus, a vaccinia virus, a parvovirus, coxsackie virus type B3, B4 and B5, and a vesicular stomatitis virus.

4. The MDCK-derived MDCKS-MG cell line of claim 3, wherein the influenza virus is A/WS/33, Initiative for Vaccine Research (IVR)-116, IVR-148, IVR-145, New York Medical College (NYMC) X-181, A/Hongkong/8/68, NYMC X-161B, NYMC X-187, NYMC X-157, IVR-147, B/Lee/40, B/Malaysia/2506/2004, B/Florida/4/2006 or B/Brisbane/60/2008.

5. A method for proliferating a virus to produce a vaccine, which comprises the steps of:
   1) infecting a Madin-Darby canine kidney (MDCK)-derived MDCKS-MG cell line (Accession No. KCLRF-BP-00297), which is suspension-cultured in a protein-free medium with the virus;
   2) culturing the MDCK-derived MDCKS-MG cell line infected with the virus; and
   3) isolating the virus from the cell culture obtained in step 2),
   wherein the protein-free medium contains serum in a concentration of 2% initially and then the concentration of serum decreases to 0% gradually.

* * * * *